United States Patent [19]

Carduck et al.

[11] Patent Number: 4,982,020

[45] Date of Patent: Jan. 1, 1991

[54] PROCESS FOR DIRECT HYDROGENATION OF GLYCERIDE OILS

[75] Inventors: Franz-Josef Carduck, Haan; Jürgen Falbe, Neuss; Theo Fleckenstein, Hilden; Joachim Pohl, Düsseldorf, all of Fed. Rep. of Germany

[73] Assignee: Henkel Kommanditgesellschaft auf Aktien, Duesseldorf, Fed. Rep. of Germany

[21] Appl. No.: 453,021

[22] Filed: Dec. 20, 1989

Related U.S. Application Data

[63] Continuation of Ser. No. 374,611, Jun. 30, 1989, abandoned, which is a continuation of Ser. No. 74,814, Jul. 17, 1987, abandoned.

Foreign Application Priority Data

Jul. 23, 1986 [DE]  Fed. Rep. of Germany ....... 3624812
Dec. 13, 1986 [DE]  Fed. Rep. of Germany ....... 3642635

[51] Int. Cl.$^5$ .................. C07C 29/136; C07C 31/125; C07C 31/20
[52] U.S. Cl. ..................................... 568/864; 568/885
[58] Field of Search ............................... 568/885, 864

[56] References Cited

U.S. PATENT DOCUMENTS

| | | | |
|---|---|---|---|
| 2,080,419 | 5/1937 | Green | 568/885 |
| 2,091,800 | 8/1937 | Adkins et al. | 568/885 |
| 2,094,127 | 9/1937 | Lazier | 260/156 |
| 2,109,844 | 3/1938 | Lazier | 260/156 |
| 2,241,417 | 3/1941 | Normann et al. | 260/638 |
| 3,173,959 | 3/1965 | Rittmeister | 568/885 |
| 3,180,898 | 4/1965 | Eisenlohr et al. | 568/885 |
| 3,363,009 | 1/1968 | Schuman et al. | 260/638 |
| 3,567,652 | 3/1971 | Moss et al. | 252/440 |
| 3,686,240 | 8/1972 | Kawada et al. | 260/409 |
| 3,699,054 | 10/1972 | Organ et al. | 252/414 |
| 3,752,773 | 8/1973 | Duke et al. | 252/454 |
| 3,856,710 | 12/1974 | Moulton et al. | 252/470 |
| 3,935,128 | 1/1976 | Fein et al. | 252/467 |
| 4,113,662 | 9/1978 | Wall | 252/473 |
| 4,134,905 | 1/1979 | Hasman | 260/409 |
| 4,158,665 | 6/1979 | Hasman | 260/409 |
| 4,158,666 | 6/1979 | Hasman | 260/409 |
| 4,169,844 | 10/1979 | Hasman | 260/409 |
| 4,199,479 | 4/1980 | Wilkes | 252/457 |
| 4,259,536 | 3/1981 | Voeste et al. | 568/885 |
| 4,282,163 | 8/1981 | Suzuki et al. | 260/409 |
| 4,433,175 | 2/1984 | Kaufhold | 568/885 |
| 4,482,766 | 11/1984 | Stoenner | 568/885 |
| 4,533,648 | 8/1985 | Corrigan et al. | 502/38 |
| 4,611,085 | 9/1986 | Kitson | 568/885 |
| 4,652,685 | 3/1987 | Cawse et al. | 568/885 |

FOREIGN PATENT DOCUMENTS 124510  11/1971  India.

OTHER PUBLICATIONS

Conner et al., "J. Am. Chem. Soc.", vol. 54 (1932), pp. 4678–4690.
W. Normann, Z. angewandte Chemie, 44 (1931), pp. 714–717.

*Primary Examiner*—J. E. Evans
*Attorney, Agent, or Firm*—Ernest G. Szoke; Wayne C. Jaeschke; Real J. Grandmaison

[57] ABSTRACT

In the direct catalytic hydrogenation of glyceride oils, the glyceride oils are continuously reacted with hydrogen under pressures of from 20 to 300 bar and at temperatures of from 160° to 250° C. with molar ratios of hydrogen to fatty acid residues in the glyceride oil substrate of from 10:1 to 500:1, the reaction being carried out over catalysts which contain from 30 to 40% by weight copper, from 23 to 30% by weight chromium, from 1 to 7% by weight barium (% by weight, based in each case on oxidic catalyst mass) and, if desired, other transition metals in the form of their oxides and which, after calcination of the components forming the catalyst mass, are converted into shaped particulate and/or granulated elements with from 1 to 10% by weight, based on oxidic catalyst, of at least one binder, and which have been activated with hydrogen or a hydrogen-containing gas mixture.

22 Claims, No Drawings

PROCESS FOR DIRECT HYDROGENATION OF GLYCERIDE OILS

This application is a continuation of Ser. No. 374,611, filed on 6/30/89, which is a continuation of Ser. No. 704,814, filed on 7/17/87, both now abandoned.

BACKGROUND OF THE INVENTION

1. Field of the Invention

This invention relates to a new process for the direct catalytic hydrogenation of glyceride oils using particulate and/or granulated catalysts containing copper chromite.

2. Statement of Related Art

The direct catalytic hydrogenation of glyceride oils has long been known from the literature. Processes such as these enable fatty alcohols—products of considerable commercial interest—to be directly obtained from fats and oils of natural origin. Hitherto, however, the process of direct hydrogenation has not been used to any significant extent in the commercial production of fatty alcohols. Instead, it has been preferred first to transesterify the glycerides of the native fats and oils with lower monoalcohols, preferably methanol, and then to subject the resulting fatty acid esters of lower alcohols to catalytic hydrogenation to form fatty alcohols. The valuable glycerol obtained in high yields and in high purity in this way ensures that the two-stage process is highly economical.

It is known from the prior art that water and propanol, rather than glycerol, are unexpectedly formed as secondary products in the one-stage process of direct hydrogenation of triglycerides (W. Nommann, Z. angewandte Chemie, 44(1931), 714–717). This is attributed to the fact that, under the prevailing reaction conditions, the glycerol initially formed enters into secondary reactions with elimination of water. The fact that it is not high-purity glycerol, but less valuable secondary products which are largely formed in the direct catalytic hydrogenation of glyceride oils by known processes means that this method of producing fatty alcohols cannot compete with the two-stage process in terms of economy. This is also the reason why the known processes for the direct hydrogenation of glyceride oils have not been adopted for working on an industrial scale.

Processes for the direct hydrogenation of triglycerides to higher aliphatic alcohols were also described in the patent literature, for example in U.S. Pat. Nos. 2,094,127; 2,109,844; and 2,241,417. In addition to the fatty alcohols corresponding in the length of the alkyl radicals to the C-chain length of the fatty acid residues, the processes disclosed in these U.S. patents, which are carried out at reaction temperatures of from 200° to 400° C. and under hydrogen pressures of from 100 to 300 bar, produce only small quantities of the desired reaction product glycerol and, instead, relatively large quantities of propane, propanol or propanediols.

German published application No. 16 68 219 describes a process for the hydrogenation of triglycerides from fats and oils, in which aluminum oxide and/or silicon dioxide catalysts promoted with iron, cobalt, molybdenum, chromium, tungsten or nickel are used for the hydrogenation at temperatures of from 300° C. to 460° C. and under pressures of up to 130 bar. This publication also mentions the danger of uncontrolled secondary reactions with formation of propylene glycol, propanol or propane instead of the valuable glycerol required. The controlled performance of the reaction at extremely high reaction temperatures and pressures is carried out to enable catalysts which, although comparatively inactive, are unaffected by catalyst poisons to be used for the hydrogenation and, in spite of this, to obtain glycerol as a secondary product. The use of copper chromite catalysts is specifically mentioned as unsuitable for the desired purposes. One disadvantage of this process is that selective product control to glycerol as a secondary product is only possible in a very narrow, but very high temperature and pressure range. Under the conditions mentioned, reduction of the fatty alcohols produced to the corresponding hydrocarbons is also observed in practice, jeopardizing the economy of the process through a reduction in yield. Another disadvantage lies in the fact that the catalysts used are not stable to traces of acid in the starting materials obtainable from native sources and, in addition, show inadequate mechanical strength, so that not only is separation of the solid catalyst from the reaction products extremely difficult, losses of active catalyst through erosion of catalyst material also have to be accepted. The need for continuous replenishment of active catalyst also jeopardizes the economy of the process.

STATEMENT OF THE INVENTION

Other than in the operating examples, or where otherwise indicated, all numbers expressing quantities of ingredients or reaction conditions used herein are to be understood as modified in all instances by the term "about".

In the context of the invention, non-deacidified glyceride oils are understood to be triglyceride mixtures of native origin which, in addition to small amounts of mono- and diglycerides, contain free fatty acids as impurities. Deacidified glyceride oils are obtained from the above-described triglyceride mixtures by separation of the free fatty acids.

It has now surprisingly been found that it is possible, using certain catalysts containing copper chromite as the principal constituent, for comparatively moderate reaction conditions, i.e. even under greatly reduced pressures, but especially with high activity and selectivity and with a long useful life of the catalysts, to control the direct hydrogenation of glyceride oils to fatty alcohols in such a way that 1,2-propanediol is formed in high yields as a valuable secondary product which can be used for the production of alkyd and polyester resins and for numerous cosmetic and pharmaceutical applications.

An object of the present invention is to provide a process for the direct catalytic hydrogenation of glyceride oils using particulate and/or granulated catalysts containing copper chromite, by which glyceride oils can be reacted directly, i.e. without any need for preliminary splitting or transesterification, even at relatively low pressures, to form fatty alcohols and 1,2-propanediol in high yields. The heterogeneous transition-metal catalyst used for the reaction leads to the required products with high activity and selectivity, without secondary reactions significantly contributing toward a reduction in the product yield. In addition to an increase in catalyst activity over standard commercial catalysts, however, the invention also seeks to improve the useful life of the catalyst. Together with the establishment of moderate reaction conditions, this should improve the economy of the process in relation to the prior art.

The present invention relates to a process for the direct catalytic hydrogenation of glyceride oils at high reaction temperatures and under high reaction pressures using particulate and/or granulated catalysts containing copper chromite as the principal constituent, wherein deacidified or non-deacidified glyceride oils are continuously reacted with hydrogen under pressures of from 20 to 300.bar and at temperatures of from 160° to 250° C. with molar ratios of hydrogen to fatty acid residues in the glyceride oil substrate of from 10:1 to 500:1, the reaction being carried out over catalysts which contain from 30 to 40% by weight copper, from 23 to 30% by weight chromium and from 1 to 7% by weight barium (% by weight, based in each case on oxidic catalyst mass) and, if desired, other transition metals in the form of their oxides, and which, after calcination of the components forming the catalyst mass, have been converted into shaped particulate and/or coarse-grained elements with from 1 to 10% by weight, based on oxidic catalyst, of at least one binder and activated with hydrogen or a hydrogen-containing gas mixture.

Glyceride oils suitable for catalytic hydrogenation by the process of the invention can be of natural or synthetic origin. In general, however, glyceride oils emanating from naturally occurring fats and/or oils are directly hydrogenated. Accordingly, suitable starting materials for the direct hydrogenation process according to the invention are the fats, train oils or oils emanating from animal or vegetable sources in which mono- or polyunsaturated fatty acids are esterified with glycerol, the fatty acid residues optionally having the same or different degrees of saturation and alkyl chain lengths. Not only individual triglycerides, but also mixtures of triglyceride oils may be directly hydrogenated by the process of the invention.

Where they originate from natural sources, the above starting materials contain more or less large amounts of free fatty acids which always adversely affected the activity of prior-art catalysts. In the process of the invention, however, it is possible to directly hydrogenate deacidified or non-deacidified glyceride oils. i.e. triglyceride oils which also contain natural levels of free fatty acids, without the free fatty acids in any way adversely affecting the activity of the catalysts used in the process of the invention. The possibility of also being able directly to hydrogenate non-deacidified glyceride oils from natural sources is one of the principal advantages of the present process. The direct hydrogenation of non-deacidified glyceride oils or mixtures thereof is a preferred embodiment of the process. Where the process of the invention for the direct catalytic hydrogenation of native glyceride oils is used, there is no longer any need for the hitherto usual steps of deacidification of the glyceride oils or mixtures thereof before the actual hydrogenation.

In the process of the invention, the direct catalytic hydrogenation of the glyceride oils is carried out in the presence of a catalyst which contains—based on the oxidic catalyst mass—from 30 to 40% by weight copper, from 23 to 30% by weight chromium, from 1 to 7% by weight barium and, optionally, other transition metals. The above metals are present in the form of their oxides after production of the catalyst masses which is carried out by methods known from the prior art. Oxide formation takes place, as known from the prior art, during the so-called "calcination," which is a thermal decomposition of mineral salts of the particular metals.

In one preferred embodiment of the process of the invention, a catalyst additionally containing from 1 to 10% by weight $SiO_2$, based on the oxidic catalyst mass, is used for the direct hydrogenation of the triglycerides.

In another preferred embodiment of the process of the invention, glyceride oils of naturally occurring fats and/or oils are continuously hydrogenated using a catalyst advantageously containing from 32 to 38% by weight copper, based on the oxidic catalyst mass. It can also be of advantage to adjust the quantity of chromium in the catalyst used to a range of from 26 to 29% by weight, the quantity of barium to a range of from 1.5 to 3% by weight or the quantity of silicon to a range of from 1.5 to 3% by weight, based in each case on the oxidic catalyst mass before activation. In one particularly preferred embodiment, a catalyst containing from 32 to 38% by weight copper, from 26 to 29% by weight chromium, from 1.5 to 3% by weight barium, from 1.5 to 3% by weight silicon and, optionally, 2.5% by weight manganese, based in each case on the oxidic catalyst mass before activation, and optionally other transition metals in the form of their oxides is used for the direct catalytic hydrogenation of the glyceride oils of natural fats or oils. With catalysts such as these, it is possible to obtain considerable increases in activity, even at relatively low pressures. For this reason, the use of a catalyst such as this in the process of the invention is regarded as particularly preferred.

In another preferred embodiment of the process of the invention, a catalyst containing other transition metals in the form of their oxides, in addition to the above-mentioned quantities of copper, chromium, barium and silicon, is used for the direct catalytic hydrogenation of the glyceride oils of native fats and/or oils. Thus, a catalyst containing from 1 to 5% by weight and preferably from 2 to 3% by weight each of one or more metals from the group: manganese, zirconium and/or cerium, in addition to the above metals can be used with advantage. In this connection, it is possible to add one of these transition metals in the form of its oxides or even several of these transition metals in the from of their oxides in admixture with one another to the catalysts used in accordance with the invention. The use of additionally doped catalysts such as these in the process of the invention leads to a considerable increase in the activity and selectivity of the catalysts, particularly where hydrogenation is carried out in a trickling bed. In particular, the 1,2-propylene glycol yield of the hydrogenation process can be distinctly increased.

Catalysts of the invention can optionally contain from 1 to 10% by weight graphite to improve the processability of the granulates and/or extrudates. A quantity of 5% by weight graphite is preferably added to and thoroughly mixed with the calcined powder-form material before granulation.

Surprisingly, it was also possible to improve the process of the invention for the direct catalytic hydrogenation of glyceride oils by increasing the activity of the catalyst in relation to that of standard commercial catalysts by optimizing not only the chemical composition of the catalyst as described above, but also the physical composition of the shaped catalyst elements. By this is meant that the physical composition of the shaped catalyst elements also has a considerable bearing on the activity and selectivity of the catalyst.

According to the invention, an improvement in the process was obtained by bringing the catalyst used containing the abovedescribed metals in the form of their oxides and graphite into granulate or extrudate form using from 1 to 10% by weight of one or more binders, preferably from 1 to 5% by weight of one or more binders. Suitable binders are compounds known for this purpose from the prior art, of which either one or even several may be used in the catalysts used in accordance with the invention. The use of one or more binders from the group: silica sol, polyvinyl acetate, and methyl methacrylate has proven to be particularly effective. In contrast to numerous, non-free-flowing catalyst materials known from the prior art, it was possible to provide a catalyst in granulate or extrudate form for the process of the invention, of which the loosened, porous structure contributes significantly towards increasing the activity and selectivity of the catalyst in the direct hydrogenation of glyceride oils, even at relatively low pressures, particularly in a trickling bed. Polyvinyl acetate is preferably used as a binder for the production of the catalyst granulates or extrudates, commercially obtainable 10% by weight polyvinyl acetate suspensions being used for example for production of the catalyst. After thorough mixing, polyvinyl acetate suspensions such as these are added in small quantities to the calcined, powder-form catalyst materials and mixed therewith until agglomerate grains begin to build up. The agglomerate-containing powder is then compacted to small granulates, for example in a perforated-roll granulator, this process being known for use with other materials from the prior art. The granulates are dried, again in known manner, to residual moisture contents of from 10 to 15%. The granulates resulting from this operation are sieved, grain fractions of a certain grain size being sieved out for use in the process of the invention. Catalyst grain fractions having a grain size of from 0.2 to 6 mm and preferably of from 0.5 to 4 mm are advantageously used where the process of the invention is used for the catalytic direct hydrogenation of glyceride oils in a trickling bed.

The catalysts can also be compressed into tablet from, for example into 4×4 mm tablets. For hardening, the tablets are tempered in air for 6 h at a temperature of 200° C. The specific surface of such tablets, as determined by the BET method (Z. Anal. Chem. 288 (1968), 187-193), was 30±10 m$^2$/g.

The granulated catalysts suitable for use in the process of the invention for the direct hydrogenation of glyceride oils have a specific surface of from 20 to 40 m$^2$/g, the preferred specific surface range being from 25 to 30 m$^2$/g. The above pregranulation processing leads to a special, loosened pore structure which increases the degree of pore utilization.

In the course of the studies leading to the process of the invention for the direct hydrogenation of glyceride oils, it was found to be of particular advantage to react the glyceride oils with hydrogen in the presence of a catalyst of which the granulates or extrudates have a diameter of from 1 to 6 mm and preferably of from 2 to 3 mm and a length of from 1 to 6 mm and preferably of from 2 to 4 mm. Granulates or extrudates (tablets) such as these show excellent activity and selectivity in the direct reaction of the glyceride oils with hydrogen to long-chain fatty alcohols and, in addition, can readily be separated from the reaction products. In addition, the useful lives obtainable with these catalysts are considerably better than the useful lives of the catalysts known from the prior art which, in addition, had the disadvantage that, in some cases, they disintegrated during the reaction and, as a result, could only be separated from the reaction products with considerable difficulty.

Another factor significantly affecting the activity and selectivity of the catalysts used in accordance with the invention is the pore volume of the shaped catalyst elements. It has been found that the pore volume of the catalysts usable in accordance with the invention must lie in an optimal range in order to produce optimal results in the process of the invention for the direct hydrogenation of glyceride oils. In one preferred embodiment of the present process, metal-containing catalysts are used having a pore volume in the range of from 0.1 to 1.0 cm$^3$/g. A pore volume in this range also has the advantage of contributing toward increasing the activity and selectivity of the hydrogenation catalysts. High activities and selectivities can be obtained both in trickling bed reactors and in sump phase reactors. At the same time, catalysts of the present type had an extremely long useful life in the process of the invention, and did not present any problems during the separation of catalyst and reaction products.

The catalysts used in the process of the invention are normally activated with hydrogen or with a hydrogen-containing gas mixture before they are used in the direct hydrogenation of glyceride oils. For economic reasons, a gas mixture predominantly consisting of a nitrogen/hydrogen gas mixture is advantageously used for activation of the catalyst masses. As known from the prior art, such activation may advantageously be carried out by drying the catalyst masses in a stream of nitrogen at elevated temperature after their production and adding hydrogen in increasing quantities to the drying gas for activation. The proportion of hydrogen in the activating gas mixture may amount to between 0.1 and 10% by volume. The activation of the catalysts may be carried out both in situ and also in vessels separate from the reaction vessel.

The reaction temperatures of the actual direct hydrogenation of non-deacidified glyceride oils of native fats and oils by the process according to the invention are in the range from 160° to 250° C. and preferably in the range from 200° to 230° C. In the temperature control of the reaction, a general factor to be taken into consideration is that the direct hydrogenation of the glyceride oils to fatty alcohols and propylene glycol is an exothermic chemical reaction. This reduction in the reaction temperature in relation to the prior art contributes towards improved economy of the process according to the invention. Accordingly, in the control of the reaction temperature, it is important to ensure that, after the reduction of the glyceride oils has "started," the heat of reaction generated is dissipated in the usual way.

One preferred range for the reaction pressures is from 20 to 49.9 bar while another preferred pressure range is from 50 to 300 bar.

One particularly preferred range for the reaction pressures is from 30 to 49.9 bar. Another highly preferred range for the reaction pressures is from 200 to 260 bar. Under reaction pressures such as these, the catalysts show high activity and selectivity so that the volume/time yield of the process of the invention is in an optimal range.

The process of the invention for the direct hydrogenation of glyceride oils of natural fats and oils is also characterized in that the molar ratio of hydrogen to fatty acid residue in the glyceride oil substrate is adjusted to a value of from 10:1 to 500:1. This means that the throughput of hydrogen gas, as measured in moles/hour, is from 10 to 500 times higher than the throughput of glyceride oil, as measured in moles of fatty acid residue/hour. A preferred range for this molar ratio is from 30:1 to 200:1, again based on fatty acid residues in the glyceride oil substrate.

The advantages of the process of the invention lie in the fact that the effectivenesss of the catalyst is clearly improved in relation to that of the prior-art catalysts through optimization both of the chemical composition and of the physical composition of the copper chromite catalysts used. In particular, improved catalyst activity and selectivity is obtained through an increase in the pore volume and degree of pore utilization of the shaped catalyst elements. In addition, the promotion of the copper chromite with barium or silicon oxide and, optionally, with other transition metal oxides leads to a further considerable increase in activity. As a result, the reaction temperatures for the direct hydrogenation of glyceride oils can be considerably reduced and, hence. The selectivity of the process improved, particularly in regard to the yield of 1,2-propylene glycol as a desirable by-product. The catalyst may be brought into a particulate form through the use of a binder and the useful life of the catalyst further improved through these shaped elements. The shaped catalyst elements obtained by granulation or extrusion show considerably better breaking hardness, do not disintegrate in the course of the hydrogenation process of the invention and do not present any problems in the separation of the reaction products from the catalyst masses.

The invention is illustrated but not limited by the following Examples.

EXAMPLE 1

Production of a catalyst:

84.93 g $Ba(NO_3)_2$, 3493 g $Cu(NO_3)_2.2\ H_2O$, 294.43 g $Mn(NO_3)_2.4\ H_2O$ and 62.3 g $SiO_2$ in the form of a 40% by weight silica sol were dissolved with vigorous stirring in 9 liters deionized water at temperatures of from 30° to 90° C. In a second vessel, 1639 g $CrO_3$ were dissolved in 9 liters deionized water under the same conditions, followed by the addition of 3650 g of a 25% ammonia solution. The solution containing barium, manganese and copper was then pumped at 30° to 90° C. into the ammonium chromate solution, a mixture of barium chromate, manganese hydroxide, silicon hydroxide and copper chromate being precipitated from the solution. Precipitation stopped when the pH value fell below 7.

The precipitate was filtered in a frame filter press and washed with deionized water until free from nitrate. The filter cake was dried overnight at 90° to 120° C. and then reduced to a coarse powder in a cutting mill. The resulting chromate powder was thermally decomposed ("calcined ) to chromite at 300° to 500° C. in a revolving tubular furnace. The calcined powder-form material had the following chemical composition:

Cu: 36±0.5%;
Cr: 29±0.5%;
Mn: 2.5±0.5%;
Ba: 1.7±0.5% and
Si: 1±0.3%.

5% by weight graphite was added to 1 liter of the powder, followed by mixing for 15 minutes in a Lodige mixer. 10% by weight of a 40% by weight polyvinyl acetate suspension were then added, followed by brief mixing until agglomerates began to build up. The powder was then compacted to small granulates in a perforated-roll granulator, dried to a residual moisture content of 10 to 15% and sieved to a 0.6 to 1.2 mm grain fraction.

The powder had excellent flow properties and was compressed in a rotary tabletting machine to tablets 3 to 6 mm in diameter and 2 to 4 mm thick.

After hardening of the tablets (6h, 200° C., in air), the specific BET surface was 40±10 $m^2/g$ for a pore volume of from 0.4 to 0.6 $cm^3/g$.

EXAMPLE 2

Production of a catalyst: 84.9 g $Ba(NO_3)_2$, 3439 $Cu(NO_3)_2.3\ H_2O$ and 62.3 g $SiO_2$ in the form of a 40% by weight silica sol were dissolved with vigorous stirring in 9 liters deionized water at temperatures of from 30° to 90° C. In another reaction vessel, 1639 g $CrO_3$ were dissolved in 9 liters deionized water under the same conditions and 3650 g of a 25% ammonia solution subsequently added. The solution containing barium and copper was then pumped at 70° C. into the ammonium chromate solution, a mixture of barium chromate, silicon hydroxide and copper chromate being precipitated from the solution. Precipitation stopped when the pH value fell below 7. The precipitate was filtered in a frame filter press and washed with deionized water until free from nitrate. The filter cake was dried overnight at 90° to 120° C. and then reduced to a coarse powder in a cutting mill. The resulting chromate powder was thermally decomposed ("calcined") to chromite at 300° to 500° C. in a revolving tubular furnace. The calcined powder-form material had the following composition:

Cu: 38±0.5%;
Cr: 29±0.5%;
Si: 1±0.3% and
Ba: 1.9±0.3%.

5% by weight graphite was added to 1 liter of the powder, followed by stirring for 15 minutes in a Lodige mixer. 10% by weight of a 40% by weight polyvinyl acetate suspension were then added, followed by brief mixing until agglomerates began to build up. The powder was then compacted to small granulates in a perforated-roll granulator, dried to a residual moisture content of 10 to 15% and sieved to a 0.6 to 1.2 mm grain fraction.

The powder had excellent flow properties and was compressed in a rotary tabletting machine to tablets 3 to 6 mm in diameter and 2 to 4 mm thick. After hardening of the tablets (6 h, 200° C., in air), the specific BET surfaces were 30±10 $m^2/g$, the pore volume 0.2 to 0.4 $cm^3/g$ and the breaking hardness of the tablets 3 to 7 kp per tablet.

EXAMPLES 3 to 6 and COMPARISON EXAMPLES 1 and 2

Coconut oil (characteristics: saponification number ((S.no.) 253; acid number (A.no.) 1.3; iodine number (I.no.) 8.7) treated with active carbon and bleaching earth was continuously reacted with hydrogen in cocurrent in a 1 liter trickling bed reactor charged with the catalyst tablets (diameter 4 mm; height 4 mm) of Example 1. After two-stage separation, excess hydrogen was recycled to the reactor together with fresh gas.

The process parameters and the results obtained are shown in Table 1 below.

TABLE 1

|  | Examples | | | | | |
| --- | --- | --- | --- | --- | --- | --- |
|  | 1 | 2 | 3 | 4 | 5 | 6 |
| Reaction pressure (bar) | 100 | 100 | 50 | 30 | 20 | 20 |
| Reaction temperature (°C.) | 200 | 240 | 220 | 220 | 220 | 240 |
| LHSV (1 × $l^{-1}$ × $h^{-1}$) | 0.5 | 1.0 | 0.5 | 0.5 | 0.5 | 0.5 |
| $H_2$:substrate (mole × mole equiv.$^{-1}$) | 200 | 100 | 200 | 200 | 200 | 200 |
| Product saponification number | 1.0 | 1.0 | 0.6 | 1.5 | 44 | 1.1 |
| Product composition (% by weight) | | | | | | |
| Fatty alcohol | 85.8 | 85.6 | 85.9 | 85.7 | 71.3 | 85.4 |
| 1,2-propanediol | 10.7 | 5.5 | 8.5 | 9.3 | 7.4 | 2.0 |
| n-/i-propanol | 0.48 | 4.8 | 2.34 | 1.64 | 1.42 | 7.79 |
| Hydrocarbons | 0.03 | 0.3 | 0.17 | 0.1 | 0.1 | 0.5 |

EXAMPLE 7

Coconut oil (characteristics: saponification number (S.no.) 255; acid number (A.no.) 16.5; hydroxyl number (OH no.) 18.5) treated with active carbon and bleaching earth was continuously reacted with hydrogen in co-current in an 8 liter, 4.2 cm diameter trickling bed reactor charged with the catalyst tablets (diameter 4 mm; thickness 4 mm) of Example 2. After two-stage separation, excess hydrogen was recycled to the reactor together with fresh gas. The hydrogen pressure was 260 bar and the reaction temperature 230° C.

The process parameters and the results obtained are shown in Table 2 below.

TABLE 2

| Reaction temperature (°C.) | 230 |
| --- | --- |
| Reaction pressure (bar) | 260 |
| LHSV (1 × $l^{-1}$ × $h^{-1}$) | 1 |
| $H_2$:oil (mole:equiv.) | 100 |
| Product appearance | water-clear |
| Product characteristics: S. no. | 1.8 |
| A. no. | 0.5 |
| Product composition (% by weight) | |
| fatty alcohols | 83.7 |
| 1,2-propanediol | 9.2 |
| $H_2O$ | 2.8 |
| methanol/ethanol | 0.5 |
| n-/i-propanol | 1.5 |
| hydrocarbons | 0.2 |

EXAMPLES 8 to 12

Coconut oil which had been pretreated in different ways was continuously catalytically hydrogenated using the catalyst prepared in accordance with Example 1 in a 1 liter trickling bed reactor (Examples 8 to 11) and in an 8 liter trickling bed reactor (Example 12). The particulars of each test and the test results obtained are shown in Table 3 below.

TABLE 3

|  | Example 8 | Example 9 | Example 10 | Example 11 | Example 12 |
| --- | --- | --- | --- | --- | --- |
| Reactor diameter (cm) | 2.5 | 2.5 | 2.5 | 4 | 4.2 |
| Quantity of catalyst (ml) | 250 | 250 | 250 | 500 | 8000 |
| Catalyst form (mm) | Tabl., 0.8–1.6 | Gran., 0.8–1.6 | Gran. 1.0 | Extr. 3 × 3 | Tabl. 4 × 4 |
| Reaction pressure (bar) | 250 | 250 | 250 | 250 | 260 |
| Reaction temperature (°C.) | 220 | 225 | 220 | 220 | 200 |
| Substrate | coconut oil (refined) | coconut oil (1) | coconut oil (refined) | coconut oil (refined) | coconut oil (refined) |
| S. characteristics | | | | | |
| S. no. | 244 | 255 | 255 | 255 | 255 |
| A. no. | 0.6 | 16.5 | 0.6 | 0.5 | 0.5 |
| I. no. | 10.25 | | | 9.3 | 9.3 |
| OH no. | 2.1 | 7.0 | 2.1 | 2.1 | 2.1 |
| LHSV (1 × $l^{-1}$ × $h^{-1}$) | 2.0 | 2.0 | 2.0 | 1.0 | 0.5 |
| $H_2$:substrate (mole/mole equiv.) | 200:1 | 200:1 | 200:1 | 100:1 | 250:1 |
| Flow rate $H_2$ (cm.$s^{-1}$) | 3.7 | 3.7 | 3.7 | 0.73 | 12.2 |
| Product appearance | water-clear | water-clear | water-clear | water-clear | water-clear |
| P. characteristics | | | | | |
| S. no. | 0.8 | 1.9 | 0.6 | 2.2 | 0.3 |
| A. no. | <1 | <1 | 0.3 | 0.25 | <0.2 |
| I. no. | 0.1 | | | | |
| OH no. | 408 | | 406 | | 400 |
| Product composition (% by weight) | | | | | |
| Fatty alcohols | 84.1 | 83.5 | 85.1 | 86.4 | 85.2 |
| 1,2-propanediol | 11.2 | 9.7 | 11.4 | 9.6 | 11.0 |
| $H_2O$ | 2.1 | 2.7 | 2.7 | 2.2 | 2.7 |
| Methanol/ethanol | <0.5 | <0.5 | <0.1 | <0.5 | <0.5 |
| n-/i-propanol | <1 | 1.5 | <0.5 | <1.0 | <0.5 |
| Hydrocarbons | <0.05 | 0.02 | 0.02 | 0.02 | 0.02 |

Note
(1): Treated with activated carbon/bleaching earth

EXAMPLES 13 and 14

A powder-form, calcined copper oxide-chromium oxide catalyst having the following composition:
Cu: 32.8%
Cr: 27.5% and Ba: 6.4%
was granulated in the same way as described in Example 2. The catalyst had a specific surface of 37.5 m²/g.

For use in Example 13, the catalyst granulate was compressed to tablets 3.0 mm in diameter and 3.0 mm thick. For use in Example 14, a fraction having grain sizes of from 0.8 to 1.6 mm was sieved out from the granulate.

In both cases, the substrate to be hydrogenated was a coconut oil treated with active carbon/bleaching earth. The continuous hydrogenation was carried out in a 1 liter, 2.5 cm diameter trickling bed reactor through which the hydrogen was passed in cocurrent with the substrate. The other process parameters and the test results are shown in Table 4 below.

TABLE 4

|  | Example 13 | Example 14 |
|---|---|---|
| Quantity of catalyst (ml) | 2000 | 250 |
| Catalyst form (mm) | Tabl. 3.0 × 3.0 | Gran. 0.8–1.6 |
| Reaction pressure (bar) | 260 | 250 |
| Reaction temperature (°C.) | 220 | 220 |
| Substrate | coconut oil (1) | coconut oil (1) |
| S. characteristics S. no. | 255 | 255 |
| A. no. | 10 | 10 |
| I. no. | — | 5.7 |
| OH no. | 6.3 | 6.3 |
| LHSV ($1 \times 1^{-1} \times h^{-1}$) | 0.5 | 1.0 |
| H$_2$:substrate (mole/mole equiv.) | 400:1 | 400:1 |
| Rate of flow H$_2$ (cm.s$^{-1}$) | 7.2 | 3.7 |
| Product appearance | water-clear | water-clear |
| P. characteristics S. no. | 4.5 | 0.9 |

TABLE 4-continued

|  | Example 13 | Example 14 |
|---|---|---|
| A. no. | 0.3 | 0.3 |
| I. no. | 0.4 | 0.4 |
| OH no. | 384 | 384 |
| Product composition (% by weight) | | |
| Fatty alcohols | 84.0 | 84.4 |
| 1,2-propanediol | 10.5 | 11.4 |
| H$_2$O | 2.8 | 2.7 |
| Methanol/Ethanol | 0.5 | 0.5 |
| n-/i-propanol | 1.0 | 0.5 |
| Hydrocarbons | 0.2 | 0.1 |

COMPARISON EXAMPLES 1 to 3

For comparison with the catalysts produced in accordance with Examples 2 and 1 and mentioned in Examples 13 and 14, conventional, commercially obtainable catalysts were tested for their activity in a trickling bed reactor (1 liter). The process parameters and the results are shown in Tables 5 and 6 below.

As a comparison of Examples 7 to 14 with Comparison Examples 1 to 3 shows, the quantity of 1,2-propanediol obtained falls well short of the theoretically obtainable quantity in all the Comparison Examples. Instead, a distinctly increased proportion of n- and i-propanol is found in the product mixture. In addition, the fatty alcohols obtained in the course of hydrogenation are to a considerable extent reduced to hydrocarbons. Accordingly, the conventional direct hydrogenation processes are distinctly inferior to the process according to the invention using the copper chromite catalysts.

TABLE 5

|  | Comparison Example 1 | Comparison Example 2 | Comparison Example 3 |
|---|---|---|---|
| Catalyst | A-carbon/2.5% Re | CuCr/Ba,Zn | Cu/Zn |
| Quantity of catalyst (ml) | 1000 | 970 | 500 |
| Catalyst form (mm) | Extrudates | Tabl., 3.13 × 3.13 | Tabl., 4 × 4 |
| Reaction pressure (bar) | 250 | 200 | 250 |
| Reaction temperature (°C.) | 250 | 270 | 220 |
| Substrate | coconut oil (1) | coconut oil (crude) | coconut oil (refined) |
| S. characteristics | | | |
| S. no. | 253.7 | 253.7 | 245 |
| A. no. | 14.1 | 14.1 | 0.5 |
| OH no. | 18.1 | 18.1 | 3.2 |
| LHSV ($1 \times 1^{-1} \times h^{-1}$) | 0.2 | 0.45 | 1.0 |
| H$_2$:substrate (mole/mole equiv.) | 560:1 | 440:1 | 100:1 |
| Flow rate H$_2$ (cm.s$^{-1}$) | 4.0 | 10.3 | 0.73 |

Note:
(1) Treated with active carbon/bleaching earth

TABLE 6

|  | Comparison Example 1 | Comparison Example 2 | Comparison Example 3 |
|---|---|---|---|
| Product appearance | water-clear/2nd aqueous phase | water-clear/2nd aqueous phase | catalyst-containing |
| P. characteristics | | | |
| S. no. | 155 | 2.0 | 49 |
| A. no. | 3.9 | 1 | 0.3 |
| OH no. | 120 | | |
| P. composition (% by weight) | | | |
| Fatty alcohols | 27.6 | 82.3 | 64.2 |
| 1,2-propanediol | 0.1 | 0.91 | 5.1 |
| H$_2$O | 0.46 | 4.0 | 2.0 |
| Methanol/ethanol | 0.5 | 0.53 | 0.5 |
| n-/i-propanol | 1.2 | 6.98 | 3.2 |

TABLE 6-continued

|  | Comparison Example 1 | Comparison Example 2 | Comparison Example 3 |
|---|---|---|---|
| Hydrocarbons | 2.46 | 2.63 | 0.04 |

We claim:

1. A process for the direct catalytic hydrogenation of glyceride oils comprising the steps of
   A. continuously reacting glyceride oils with hydrogen gas at a pressure of from about 20 to about 300 bar and a temperature of from about 160° to about 250° C., at a molar ratio of hydrogen to fatty acid residues in the glyceride oil of from about 10:1 to about 500:1 in the presence of a calcined oxidic catalyst containing from about 30 to about 40% by weight copper, from about 23 to about 30% by weight chromium, and from about 1 to about 7% by weight barium, the percentages by weight being based on the total weight of oxidic catalyst, said calcined oxidic catalyst having then been mixed with from about 1 to about 10% by weight of a binder and with from about 1 to about 10% by weight of graphite, based on the weight of said oxidic catalyst, until agglomerate particles are formed and then shaped into particulates or granulates having a specific surface of from about 20 to about 40 m$^2$/g., a diameter of from about 1 to about 6 mm, a length of from about 1 to about 6 mm, and a pore volume of from about 0.1 to about 1.0 cm$^3$/g., and then activated by hydrogen or a hydrogen-containing gas, to form a reaction product containing long chain alcohols and propylene glycol, and
   B. separating the long chain alcohols and propylene glycol from the catalyst.

2. The process of claim 1 wherein in step A the hydrogenation is carried out at a pressure of from about 20 to about 49.9 bar.

3. The process of claim 1 wherein in step A the hydrogenation is carried out at a pressure of from about 50 to about 300 bar.

4. The process of claim 1 wherein the catalyst also contains from about 1 to about 10% by weight of silicon based on the total weight of the oxidic catalyst.

5. The process of claim 1 wherein the glyceride oils are non-deacidified glyceride oils of natural fats or oil.

6. The process of claim 5 wherein the catalyst contains from about 32 to about 38 percent by weight of copper.

7. The process of claim 5 wherein the catalyst contains from about 26 to about 29 percent by weight of chromium.

8. The process of claim 5 wherein the catalyst contains from about 1.5 to about 3 percent by weight of barium.

9. The process of claim 5 wherein the catalyst contains from about 1.5 to about 3 percent by weight of silicon.

10. The process of claim 5 wherein the catalyst contains from about 32 to about 38 percent by weight of copper, from about 26 to about 29 percent by weight of chromium, from about 1.5 to about 3 percent by weight of barium, and from about 1.5 to about 3 percent by weight of silicon.

11. The process of claim 10 wherein the catalyst also contains about 2.5 percent by weight of manganese.

12. The process of claim 5 wherein the catalyst contains from about 32 to about 38 percent by weight of copper, from about 26 to about 29 percent by weight of chromium, from about 1.5 to about 3 percent by weight of barium, from about 1.5 to about 3 percent by weight of silicon, and from about 1 to about 5 percent by weight of at least one of manganese, zirconium, and cerium.

13. The process of claim 12 wherein from about 2 to about 3 percent by weight of at least one of manganese, zirconium, and cerium are present.

14. The process of claim 1 wherein the binder is one or more of polyvinyl acetate, methylmethacrylate and silica sol.

15. The process of claim 5 wherein from about 1 to about 5 percent by weight of graphite is present in the catalyst.

16. The process of claim 1 wherein the diameter of the catalyst is from about 2 to about 3 mm and the length thereof is from about 2 to about 4 mm.

17. The process of claim 1 wherein the specific surface is from about 25 to about 30 m$^2$/g.

18. The process of claim 1 wherein the catalyst was activated with a nitrogen/hydrogen gas mixture containing from about 0.1 to about 10 percent by volume of hydrogen.

19. The process of claim 1 wherein the reaction pressure is from about 30 to about 49.9 bar.

20. The process of claim 1 wherein the reaction pressure is from about 200 to about 260 bar.

21. The process of claim 1 wherein the reaction temperature is in the range of from about 200° to about 230° C.

22. The process of claim 1 wherein the ratio of hydrogen to fatty acid residue in the glyceride oil is from about 30:1 to about 200:1.

* * * * *